United States Patent [19]

Marshall, Sr.

[11] Patent Number: 4,838,866

[45] Date of Patent: Jun. 13, 1989

[54] LIQUID PUMP AIR RELEASE SYSTEM

[76] Inventor: William M. Marshall, Sr., Rte. 1, Box 156, Salem, Va. 24153

[21] Appl. No.: 941,049

[22] Filed: Dec. 15, 1986

Related U.S. Application Data

[63] Continuation-in-part of Ser. No. 914,809, Oct. 3, 1986, Pat. No. 4,758,227.

[51] Int. Cl.[4] .................................................. A61M 5/00

[52] U.S. Cl. ...................................... 604/152; 604/236; 604/247; 604/122; 417/443

[58] Field of Search ............... 604/156, 152, 154, 131, 604/236, 247, 122, 124, 125; 417/520, 443

[56] References Cited

U.S. PATENT DOCUMENTS

| | | | |
|---|---|---|---|
| 3,051,173 | 8/1962 | Johnson et al. | 604/156 X |
| 3,288,072 | 11/1966 | McKenzie | 417/520 X |
| 3,957,052 | 5/1976 | Topham | 604/236 |

*Primary Examiner*—Stephen C. Pellegrino
*Attorney, Agent, or Firm*—John F. C. Glenn

[57] ABSTRACT

Air entrained in a pumped liquid is released from a pumping chamber operated by a single piston and having an outlet passage controlled by a back-seating valve biased closed by a spring, when the piston near the end of its compression stroke causes positive mechanical engagement to open the outlet valve.

6 Claims, 3 Drawing Sheets

LIQUID PUMP AIR RELEASE SYSTEM

Continuation-in-part of application Ser. No. 06/914,809 filed Oct. 3, 1986, now U.S. Pat. No. 4,758,227 issued July 19, 1988 by Gordon J. Lancaster, Jr. et al.

BACKGROUND OF THE INVENTION

Hand-held syringes have long been used for injecting chickens with antibiotics and the like. The risks and dangers of accidental injection of the operators have led to development of mechanized injection equipment such as that described in co-pending patent application Ser. No. 06/779,221 filed Sept. 24, 1985 by Gordon J. Lancaster, Jr. et al. When a conventional syringe is used in mechanized injection equipment, it has been found that air can become trapped in the compression chamber of the syringe, with the result that the power stroke of the syringe piston merely compresses the air instead of forcing the treating liquid out through the injecting needle, and the return stroke fails to develop the reduced pressure needed to recharge the syringe. A like problem can be encountered in the injector pump of a diesel engine.

SUMMARY OF THE INVENTION

In accordance with the present invention, in a syringe or other injector pump having an outlet valve resiliently biased shut, means are provided for positively pressing the outlet valve partially open as the operating piston approaches the end of its pressure stroke. This permits release of air trapped in the pressure chamber as the piston completes its stroke. One preferred means for this purpose is a rigid element mounted on the piston to project towards the outlet valve and push it open near the end of the compression stroke.

BRIEF DESCRIPTION OF THE DRAWINGS

The accompanying drawings, semi-schematically illustrate present preferred apparatus of the invention as follows.

DETAILED DESCRIPTION OF PRESENT PREFERRED EMBODIMENT

Figure 1:
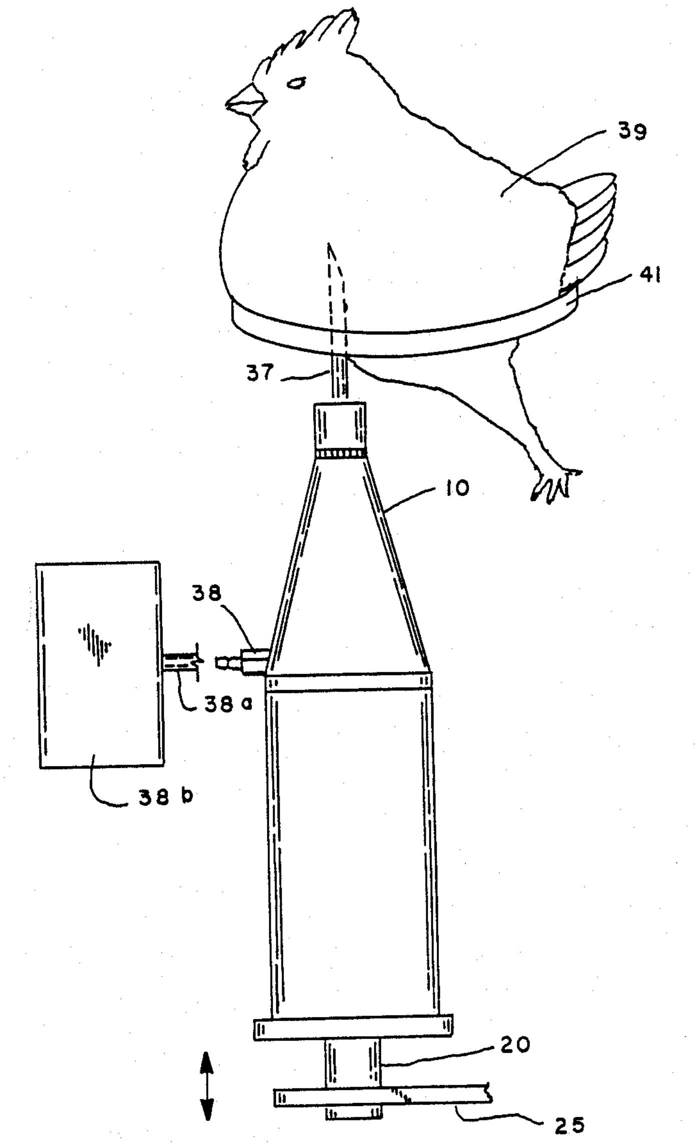
FIG. 1 shows a syringe carrying an injection needle inserted into a chicken breast.
Figure 2:
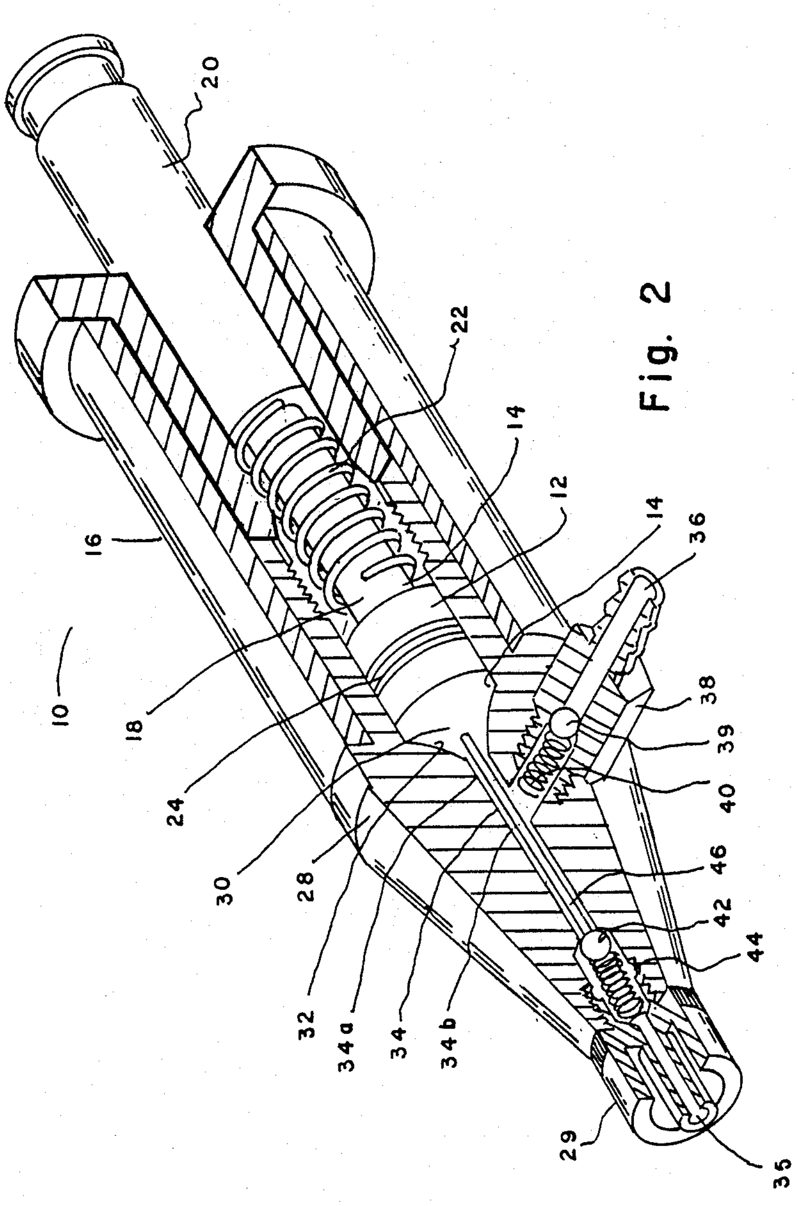
FIG. 2 shows an enlarged and partially sectioned view of the syringe shown in FIG. 1.

Referring now to the accompanying drawings, there is shown a syringe 10 having a plunger in the form of a piston 12 mounted to reciprocate in a bore 14 through a syringe body 16 on a fixed mount (not shown). The back of the piston is secured to a piston rod 18 slidable through a hollow cylindrical sleeve 20 removably secured in the body 16. A compression spring 22 extends around the rod 18 and engages the back of the piston and the inner end of sleeve 20 for resiliently pressing the piston away from sleeve 20. An O-ring 24 around the piston opposes escape of fluid past the piston along bore 14. A drive connection 25 reciprocates piston rod 18 by drawing it back against spring 22 during the return stroke and permitting spring 22 to move rod 18 and piston 12 forward during the compression stroke.

The syringe body 16 has a removable end piece 28 in which bore 14 is formed. A coupling 29 is mounted on end piece 28 for receiving the base of an injection needle. A compression chamber 30 is formed in end piece 28 in the space between the front end of piston 12, the piston of bore 14 in which the piston moves, and a conical wall 32 formed in end piece 28 to close the inner end of bore 14. The large end of conical wall 32 joins the inner end of bore 14, and the small end of conical wall 32 connects with one end of a passage 34 extending through end piece 28 parallel to the direction of movement of piston 12. An inlet passage 36 extends through end piece 28 and a fitting 38, and opens into passage 34 near its entry into compression chamber 30. The part of passage 34 between its connection with inlet passage 36 and compression chamber 30 forms a two-way passage **34*a*. The other part of passage 34 forms a one-way outlet passage 34*b* connecting with a passage 35 through coupling 29**.

The outer end of inlet passage 36 extends through fitting 38 and connects through tube **38*a* to a supply container 38*b*** for the liquid selected for injection. The supply liquid is preferably at substantially atmospheric pressure.

The outer end of outlet passage **34*b* is connected to eject fluid through an injection needle 37 mounted on coupling 29. Needle 37 is adapted to be inserted into the breast muscle of a chicken 39 positioned on a fixed support 41 when syringe 10** is mechanically propelled toward the support for that purpose.

A cheek valve ball 38 is pressed by a spring 40 to back seat in inlet pasage 37. A check valve ball 42 is pressed by a spring 44 to back seat in outlet passage **34*b***.

The spring 40 is on the compression chamber side of ball 38. Thus, ball 38 back seats to close inlet passage 36 while pressure is higher from the compression chamber side than from the other side of the ball as a result of forward movement of piston 12 toward conical wall 32. During the return movement of the piston pressure is reduced in the compression chamber until it is enough less than the pressure of resupply fluid on the other side of ball 38 to overcome spring 40 and thereby release ball 38 to admit a recharge of the selected injection fluid through passageways 36 and **34*a* into chamber 30**.

The spring 44 is on the other side of ball 42 from the compression chamber 30, and operates to back seat ball 42 to close outlet passage **34*b* at the beginning of the return stroke of piston 12. The front end of piston 12 carries an integrally secured rod 46 extending parallel to the direction of movement of the piston and adapted to engage ball 42 to press it open against spring 44 when the piston approaches the end of its forward travel in bore 14 (for example, in about the last 3% of travel). As a result, if the compression chamber 30 is full of liquid at the start of the pressure stroke, the incompressability of the liquid will cause it to press open ball 42 to begin ejection early in the stroke. However, if there is a large enough cushion of air in chamber 30, and if there is enough combined back pressure of spring 44 and the resistance to ejection from the needle of the part of the chicken in which it is embedded (such as a breast muscle), the ball 42 will remain seated until pressure has built up enough to cause at least a good part of the air to come out through passage 34 and needle 37 when rod 46 causes ball 42 to open. Otherwise, in the absence of rod 46, the air would not pass ball 42 on the pressure stroke, and on the return stroke not enough vacuum would develop in chamber 30 to cause a recharge of liquid to come in through inlet passages 36 and 34*a***.

Figure 3:
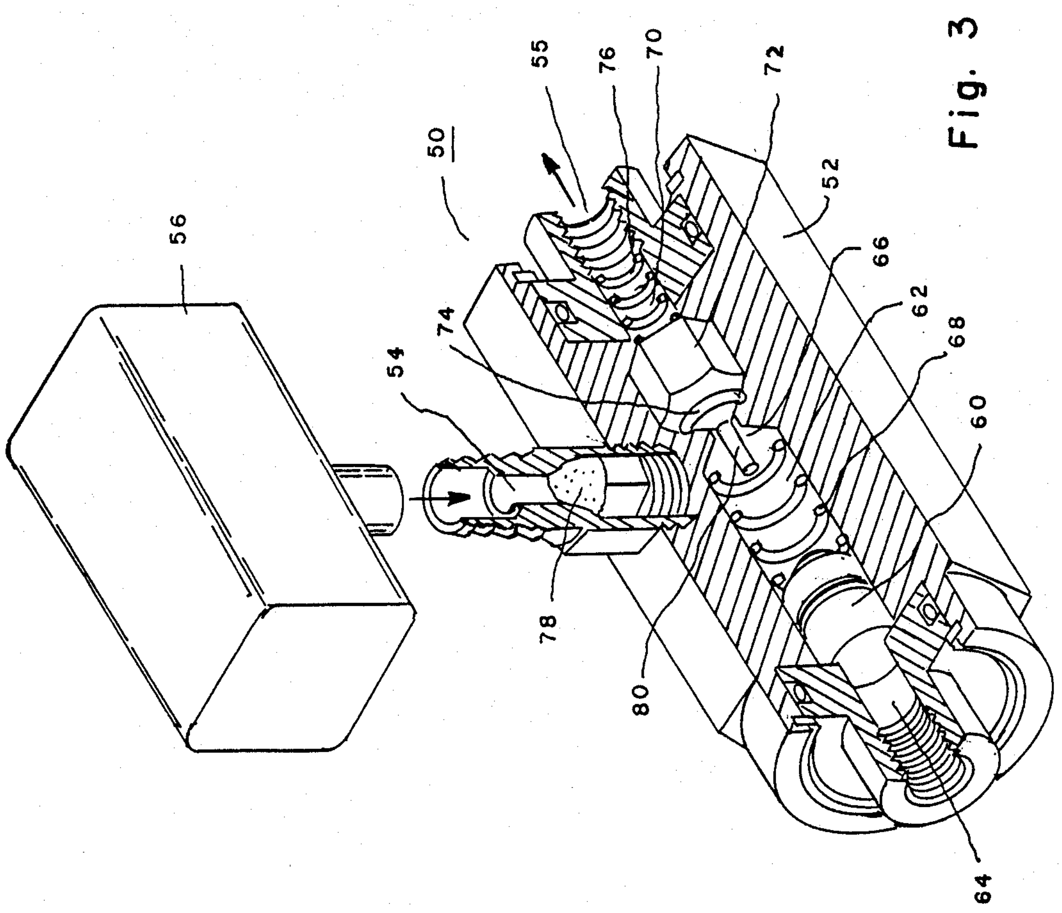
FIG. 3 shows a fuel tank drain pump such as used for a truck diesel motor.

The invention has other applicationsm, such as a drain pump for a fuel tank, such as on a diesel powered truck. For example, as shown in FIG. 3, such a pump 50 has a body 52, an inlet passage 54 connected to receive fuel from a tank 56, and an outlet passage 58 connected to discharge to the atmosphere. A piston 60 reciprocates in a piston chamber 62 in the body 50. Compressed air fed periodically through an inlet passage 64 exerts pressure on the back of piston 60 to drive it forward toward a piston chamber outlet passage 66. A spring 68 in the piston chamber drives piston 60 back again when the compressed air pressure is relieved. Another cylindrical chamber 70 in body 10 is connected with piston chamber 62 through the said outlet 66. A hexagonal member 72 is mouned to slide in chamber 70 and carries an O-ring 74 which seals against outlet 66 under the pressure of a spring 76 against member 72 when spring 68 drives piston 60 back to its retracted position.

Flow of fuel from tank 56 through inlet 54 passes a spring-pressed back-seating check valve 78 when spring 68 retracts piston 60 and O-ring 74 seals. When compressed air is again admitted through inlet 64, it drives piston 60 forward, thereby closing valve 78, releasing O-ring 74 from outlet 66, and expelling the contents of piston chamber 62 through outlet 66, past member 72 and out through outlet 58. Thus far, the structure and operation of pump 50 is conventional. The purpose is to bleed off small increments of fuel with possible water in the bottom of a fuel tank, in order to guard against accumulation of water and thereby protect the motor, especially in the case of diesel engines.

In accordance with the present invention, a rod 80 is mounted on member 74 to extend through outlet 66 far enough to be engaged by piston 60 after it has completed about 97% of its forward stroke. If the piston chamber is full of liquid in the first place, the pressure generated by forward movement of the piston will move member 72 back before the piston strikes the projecting end of rod 80. However, if enough air has accumulated in the piston chamber, it will compress and thereby interfere with expulsion of liquid in the piston chamber, in the absence of rod 80. The presence of rod 80 permits enough of the compressed air to escape, so that on the next power stroke of the piston the liquid then in the piston chamber will be discharged.

While a present preferred method and practice of the invention has been illustrated and described, it will be understood that the invention may be otherwise embodied and practiced without the scope of the following claims.

I claim:

1. A pump for drawing in a liquid charge and ejecting it against substantial superatmospheric back pressure, comprising a closed chamber, a piston reciprocable as a single unit in the chamber, said piston being the only piston in the chamber, means mechanically connected to the piston to reciprocate it in the chamber, an inlet passage and an outlet passage connecting with the chamber, inlet valve means adapted to back seat to close the inlet passage during the compression stroke of the pison and oppositely movable to open the inlet passage, outlet valve means adapted to back seat to close the outlet passage during the return stroke of the piston and oppositely movable to open the outlet passage, resilient means biasing the outlet valve means closed, and means movable by the piston and adapted to cause a mechanical engagement which positively presses the outlet valve means open and which initiates such opening of the outlet valve near the end of the compression stroke of the piston, thereby positively opening the outlet valve means and thus facilitating escape of any air which might otherwise remain in the chamber.

2. A pump according to claim 1, in which said means movable by said piston is secured to the piston.

3. A pump according to claim 1, in which said means movable by the piston is secured to said outlet valve means and is engageable by said piston near the end of its compression stroke.

4. A syringe comprising a pump according to claim 1, and an injection needle connected to the pump outlet passage.

5. A fuel tank with drain means comprising a pump according to claim 1.

6. A pump according to claim 1, in which the means movable by the piston is adapted to initiate pressing the outlet valve means open and when the piston has completed about 97 percent of its compression stroke.

* * * * *